(12) United States Patent
Vogt

(10) Patent No.: US 9,775,595 B2
(45) Date of Patent: Oct. 3, 2017

(54) KNEE SPACER SYSTEM WITH ADJUSTABLE SEPARATOR

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 366 days.

(21) Appl. No.: 14/330,735

(22) Filed: Jul. 14, 2014

(65) Prior Publication Data

US 2015/0018832 A1   Jan. 15, 2015

(30) Foreign Application Priority Data

Jul. 15, 2013   (DE) ........................ 10 2013 213 831

(51) Int. Cl.
*A61B 17/58* (2006.01)
*A61B 17/60* (2006.01)
(Continued)

(52) U.S. Cl.
CPC .............. *A61B 17/025* (2013.01); *A61F 2/38* (2013.01); *A61F 2/3836* (2013.01);
(Continued)

(58) Field of Classification Search
CPC ................ A61B 17/025; A61B 17/154; A61B 2017/0268; A61F 2/38; A61F 2/3836; A61F 2/3859; A61F 2/389; A61F 2/4684
(Continued)

(56) References Cited

U.S. PATENT DOCUMENTS 5,733,292 A * 3/1998 Gustilo ................ A61B 17/025
606/86 R
5,938,698 A   8/1999 Sandoz et al.
(Continued)

FOREIGN PATENT DOCUMENTS

CN   102088931 A   6/2011
EP     1274374 A1   1/2003
(Continued)

OTHER PUBLICATIONS

Hovelius, L., et al, "An Alternative Method for Exchange Operation of Infected Arthroplasty", Acta Orthop., 1979, pp. 93-96, vol. 50, Acta Orthop., Munksgaard, Copenhagen.
(Continued)

*Primary Examiner* — Si Ming Ku
(74) *Attorney, Agent, or Firm* — Norris McLaughlin & Marcus PA

(57) ABSTRACT

The invention relates to a knee spacer for temporary replacement of an artificial knee joint, whereby the knee spacer comprises a tibial component (11) and a separator (12), whereby the tibial component (11) comprises a running surface (14) by means of which the tibial component (11), in the patient-inserted state, can be placed against a femoral component (28) in mobile manner, and whereby the separator (12) comprises a contact surface (15) for placing on the tibia (22) and the contact surface (15) is adjustable at a variable distance from the running surface (14) of the tibial component (11).

Figure 1:
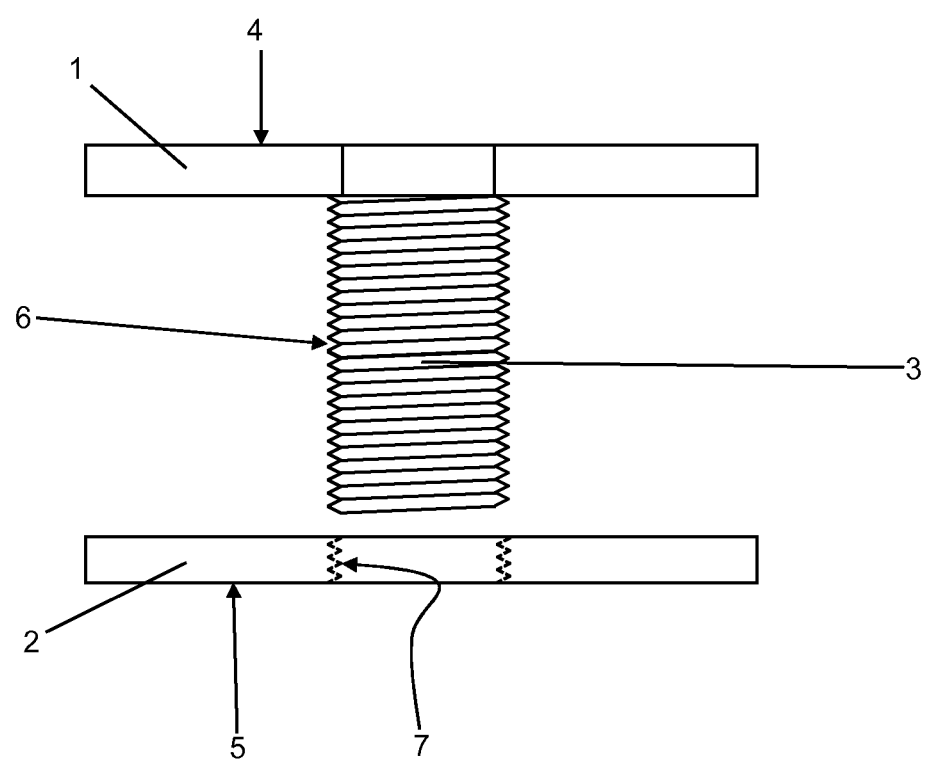

The invention also relates to a method for adapting a knee spacer to a treatment scenario, comprising a tibial component (11) and a separator (12), whereby the tibial component (11) comprises a running surface (14) for placing against a femoral component (28) in mobile manner, and the separator (12) comprises a contact surface (15) for placing on the tibia
(Continued)

(22), whereby the method involves adjusting the distance between the contact surface (15) and the running surface (14).

The invention also relates to the use of a knee spacer of this type as temporary place-holder in a knee of a patient.

9 Claims, 5 Drawing Sheets

(51) Int. Cl.
*A61F 2/00* (2006.01)
*A61B 17/02* (2006.01)
*A61F 2/38* (2006.01)
*A61F 2/46* (2006.01)
*A61F 2/30* (2006.01)

(52) U.S. Cl.
CPC .... *A61F 2/4684* (2013.01); *A61B 2017/0268* (2013.01); *A61F 2002/30672* (2013.01)

(58) Field of Classification Search
USPC .............................................. 606/90, 92–94
See application file for complete search history.

(56) References Cited

U.S. PATENT DOCUMENTS

| | | | |
|---|---|---|---|
| 6,482,209 B1 | 11/2002 | Engh et al. | |
| 7,601,176 B2* | 10/2009 | Soffiati | A61F 2/38 623/18.11 |
| 8,097,039 B2* | 1/2012 | Evans | A61F 2/30942 623/20.14 |
| 8,974,538 B2* | 3/2015 | Teeny | A61F 2/38 606/60 |
| 8,986,386 B2* | 3/2015 | Oglaza | A61B 17/7065 606/105 |
| 2006/0111790 A1 | 5/2006 | Dietz | |
| 2008/0188937 A1 | 8/2008 | Ribic | |
| 2012/0185053 A1 | 7/2012 | Berger | |
| 2013/0071872 A1 | 3/2013 | Ho et al. | |
| 2013/0073049 A1 | 3/2013 | Faccioli et al. | |
| 2013/0204267 A1 | 8/2013 | Dietz | |
| 2014/0276858 A1* | 9/2014 | Major | A61B 17/157 606/88 |

FOREIGN PATENT DOCUMENTS

| | | |
|---|---|---|
| JP | 11513274 A | 11/1999 |
| JP | H11513274 A | 11/1999 |
| WO | 9709939 A1 | 3/1997 |
| WO | 01/76512 A1 | 10/2001 |
| WO | 2010/015877 A1 | 2/2010 |
| WO | 2010015877 A1 | 2/2010 |
| WO | 2010023062 A2 | 3/2010 |

OTHER PUBLICATIONS

Younger, A.S.E., et al, "The Outcome of Two-stage Arthroplasty Using a Custom-made Interval Spacer to Treat the Infected Hip", 1997, Journal of Arthroplasty, vol. 12, pp. 615-623, University of British Columbia, British Columbia, Canada.
Jones, W. A., et al, "Salvage of Failed Total Knee Arthroplasty: The 'Beefburger' Procedure", 1989, The Journal of Bone and Joint Surgery, BR 71-B, pp. 856-857, British Editorial Society of Bone and Joint Surgery, Liverpool, England.
Cohen, J. C., et al, "Two-stage Reimplantation of Septic Total Knee Arthroplasty, Report of Three Cases Using an Antibiotic-PMMA Spacer Block", 1988, Journal of Arthroplasty, pp. 369-377, vol. 3, Michael Reese Hospital and Medical Center, Chicago, Illinois.
McPherson, E. J., et al, "Techniques in Arthroplasty, Use of an Articulated PMMA Spacer in the Infected Total Knee Arthroplasty", The Journal of Arthroplasty, 1995, vol. 10 No. 1, pp. 87-89, USC School of Medicine, Los Angeles, California.
Australian Office Action for corresponding Australian Application No. 2014203674 dated Oct. 28, 2014.
European Search Report for corresponding EP Application No. 14174580.2 dated Dec. 1, 2014.
English translation of JP Office Action for corresponding application JP 2014-145220 dated May 11, 2015.
Japanese Office Action and English language translation for corresponding application JP 2014-145220 dated Jan. 5, 2016.
EP Search Report for corresponding application EP 14 17 4580 dated Nov. 21, 2014.
Chinese Office Action and English language translation for corresponding application CN 201410336647.1 dated Nov. 30, 2015.
Canadian Office Action for corresponding applicaion CA 2855201 dated Jul. 14, 2015.
German Search Report for DE 10 2013 213 831.8 dated Apr. 8, 2014.
Chinese Office Action and Translation for corresponding application CN 201410336647.1 dated Oct. 9, 2016.

* cited by examiner

KNEE SPACER SYSTEM WITH ADJUSTABLE SEPARATOR

The invention relates to a knee spacer for temporary replacement of an artificial knee joint. The invention also relates to a method for adapting a knee spacer to a treatment scenario, comprising a tibial component and a separator, whereby the tibial component comprises a running surface for touching against a femoral component in mobile manner and the separator comprises a contact surface for placing on the tibia. The invention also relates to the use of a knee spacer of this type as temporary place-holder in a knee of a patient.

The subject matter of the invention is an articulating knee spacer system composed of a tibial component and a separator and preferably a femoral component as well. The knee spacer system is used as temporary place holder in the scope of two-stage septic revision surgeries of knee endoprostheses.

Articular endoprostheses currently have a service life of several years, for example on average more than ten and up to fifteen years in the case of cemented hip endoprostheses. However, undesirable loosening of the articular endoprostheses can occur before the end of the usual service life. This can concern either septic or aseptic loosening. Aseptic loosening means that no microbial germs are detectable yet. There are many causes of aseptic loosening. Aseptic loosening is often related to abrasion at the sliding surfaces of articular endoprostheses.

The loosening process in septic loosening is induced by microbial germs. This can either be early or late infections depending on the time of manifestation. Septic loosening is a very serious disease for the patient and its treatment is very expensive. It is customary to perform a revision surgery in cases of aseptic and septic loosening alike. This can proceed as a one-stage or a two-stage revision surgery. Two-stage revision surgeries are very common in cases of septic loosening.

In a two-stage revision surgery, the infected articular endoprosthesis is removed in a first surgery (OP) followed by debridement (removal of the infected tissue) and subsequent insertion of a temporary place-holder, a so-called spacer. Said spacer occupies for a number of weeks the space previously occupied by the revised endoprosthesis until the manifest infection has subsided. Said place-holder function is very important in order to effectively prevent muscular atrophy during this period of time and in order to stabilise the existing resection scenario.

There are non-articulating and articulating spacers available. Articulating spacers replicate the function of the joint and allow the afflicted limbs to have a certain degree of mobility. This allows the patient to be mobilised early. Therefore, the insertion of articulating spacers is very popular to date. The spacer is removed in a second surgery, another debridement is done before implanting a cemented or cement-free revision articular endoprosthesis.

The use of spacers is originally based on the work of Hovelius and Josefsson (Hovelius L, Josefsson G (1979), "An alternative method for exchange operation of infected arthroplasty", Acta Orthop. Scand. 50: 93-96). Other early work on spacers includes Younger (Younger A S, Duncan C P, Masri B A, McGraw R W (1997), "The outcome of two-stage arthroplasty using a custom-made interval spacer to treat the infected hip", J. Arthroplasty 12: 615-623), Jones (Jones W A, Wroblewski B M (1989), "Salvage of failed total knee arthroplasty: the 'beefburger' procedure", J. Bone Joint Surg. Br. 71: 856-857), and Cohen (Cohen J C, Hozack W J, Cuckler J M, Booth R E Jr (1988), "Two-stage reimplantation of septic total knee arthroplasty, Report of three cases using an antibiotic-PMMA spacer block", J. Arthroplasty 3: 369-377). McPherson described a concept according to which spacers can be manufactured from bone cement exclusively (McPherson E J, Lewonowski K, Dorr L D (1995), "Techniques in arthroplasty. Use of an articulated PMMA spacer in the infected total knee arthroplasty", J. Arthroplasty 10: 87-89).

Knee spacers equipped with antibiotics for temporary replacement of knee endoprostheses are available on the market. Knee spacers generally consist of two components, i.e. a tibial component and a femoral component. A spacer or spacer system typical of this type is known from EP 1 274 374 A1. Referring to knee spacers, in addition, both the tibial component and the femoral component need to be anchored to the proximal tibia and the distal femur using polymethylmethacrylate bone cement. In this context, the polymethylmethacrylate bone cement (PMMA bone cement) adheres to the surface of the spacer components. The surface of the spacer components, which usually consist of cured, antibiotics-doped polymethylmethacrylate bone cement, is dissolved to a certain degree by the methylmethacrylate of the polymethylmethacrylate bone cement. This leads to a bond being established to the curing polymethylmethacrylate bone cement. This is the main foundation of the adhesion of the polymethylmethacrylate bone cement to the surface of the spacer components.

Spacers, including knee spacers, are often shaped from cement dough by the physician in the course of a surgery or are cast by the physician using elastic silicone moulds. Alternatively, industrially produced spacers have been commercially available in a range of standard sizes for a number of years. Said pre-made spacers can be implanted directly by the physician without any extensive preparatory work, whereby the spacers are usually affixed to the bone tissue with polymethylmethacrylate bone cement. The advantage of industrially produced spacers is that the surface quality of the running surfaces (often referred to as sliding surfaces as well) of the pre-made spacers is generally markedly better than that of spacers produced intra-operatively. Moreover, using pre-made spacers can save valuable surgery time and simplifies the entire surgical process markedly since the time-consuming and laborious step of spacer production is omitted.

In septic revision surgeries of knee endoprostheses, the radical debridement often leads to a marked loss of bone tissue. Upon massive loss of bone at the proximal tibia in the scope of a two-stage revision, the femoral component and the tibial component of articulating spacers can temporarily substitute for the function of the joint only if the bone tissue missing on the underside of the tibial plateau is being replaced by bone cement layers of several millimeters in thickness such that the original height of the tibial plateau is approximately re-established for articulation of the femoral component with the tibial component according to the anatomy of the patient to be feasible. Said height adjustment is difficult to do for the surgeon since the cement dough used for fixation of the tibial component is subject to possible plastic deformation during the processing phase and also at the start of the curing phase of the bone cement, which might change the distance between the tibial component and the proximal component in undesired manner.

Accordingly, it is the object of the invention to overcome the disadvantages of the prior art. In particular, the invention is to provide a stable knee spacer that can be used to produce a robust and treatment setting-adaptable connection to the tibia. Specifically a loss of bone tissue due to earlier debridement is to be compensated in the treatment setting. The invention is to provide a knee spacer and/or a tibial component, which shall be referred to as knee spacer presently even in the absence of a femoral component and can be used to restore the anatomical geometry of a knee joint of a patient. Moreover, the knee spacer is to be inexpensive to manufacture. Accordingly, the invention is based on the object to develop a knee spacer system enabling the distance between the proximal tibia and the tibial component (or, specifically, the running surface of the tibial component) to be adjusted safely without there being a possibility of the distance changing during the fixation of the tibial component with polymethylmethacrylate bone cement.

The objects of the invention are solved by a knee spacer for temporary replacement of an artificial knee joint, whereby the knee spacer comprises a tibial component and a separator, whereby the tibial component comprises a running surface by means of which the tibial component, in the patient-inserted state, can be placed against a femoral component in mobile manner, and whereby the separator comprises a contact surface for placing on the tibia and the contact surface is adjustable at a variable distance from the running surface of the tibial component.

While the knee spacer is being affixed to the tibia of the patient, a layer of bone cement is arranged between the contact surface and the tibial plateau and affixes the separator to the tibia after the bone cement is cured. Therefore, according to the scope of the invention, the separator does not rest on the tibia and/or tibial plateau directly, but rather there is a layer of bone cement disposed between the separator and the tibial plateau. Said layer can be used by the physician to fine-tune the distance between the running surface and the tibial plateau.

The objects of the invention are also solved by an articulating knee spacer system that is composed of a tibial component and a separator and preferably also of a femoral component, whereby the distance between the proximal side (the running surface) of the tibial component and the distal side (the contact surface) of the separator is adjustable.

The patient-inserted state shall be defined to be the arrangement, in which the components of the knee spacer are to be or are cemented in the knee of the patient in order to form a functional, i.e. mobile, temporary implant.

Knee spacers according to the invention preferably have a stem with an external thread arranged on the side of the tibial component opposite from the running surface, whereby the separator comprising at least one feed-through is or can be screwed onto the stem by means of an internal thread that fits with the external thread of the stem such that the distance between the running surface and the contact surface is adjustable by screwing the separator onto the stem.

As an alternative to said embodiment, the invention could just as well provide, for adjusting the distance between the running surface and the contact surface, that the stem comprises multiple recesses along the distance from the running surface, whereby the separator can be affixed at different distances by means of a bolt or other locking means that engages the recesses. However, according to the invention, the variant equipped with an external thread is particularly preferred since it allows the separator to be adjusted at very many different distances from the running surface in simple and inexpensively implemented manner.

Moreover, the invention can provide the knee spacer to comprise a femoral component having a running surface, whereby the femoral component and the tibial component are present as separate components, which are mobile with respect to each other in the patient-inserted state, whereby the tibial component and the femoral component can be placed against each other in mobile manner in the patient-inserted state by means of their running surfaces.

Accordingly, it is preferred according to the invention to right away enclose a fitting femoral component with the tibial component and the separator in the form of a kit. This is advantageous in that the two components are right away matched to each other and that matching running surfaces can thus be guaranteed.

A refinement of the invention proposes the separator to comprise a disc, preferably a plane-parallel disc, whereby one side of the disc forms the contact surface.

It is particularly preferable for the separator to be a disc of this type having an opening, in which an internal thread is arranged, such that the plane-parallel disc can be screwed onto the stem equipped with the external thread.

A plane-parallel disc is particularly easy to fabricate such that said embodiment is particularly inexpensive to implement.

Moreover, the invention can provide one or more opening(s) to be situated in the contact surface of the separator through which a bone cement can extend by means of which the separator is or is to be affixed on the tibia.

By this means, the separator and thus the knee spacer can be connected more firmly to the tibia since the bone cement for fixation of the separator flows through and reaches through the opening or openings.

According to a preferred embodiment, the invention can provide the knee spacer to consist of a biocompatible material, preferably of cured polymethylmethacrylate bone cement containing at least one antibiotic and/or at least one antiseptic.

Said materials are particularly well-suited for use in the human body. Preferably, the bone cement used to affix the component and/or components of the knee spacer is the same as the bone cement of which the tibial component and the separator and, if applicable, the femoral component is/are made. However, for certain applications the invention can provide the polymethylmethacrylate bone cement (PMMA bone cement) of which the knee spacer consists to have a different composition, in particular different antibiotics and/or antiseptics.

For implementation of knee spacers according to the invention, the invention can provide the tibial component and, if applicable, the femoral component to be made of, inter alia, at least one plastic material and/or metal, preferably to consist of a plastic material and/or metal, particularly preferably of polymethylmethacrylate, even more particularly preferably of antibiotics-doped cured polymethylmethacrylate bone cement.

Said materials are particularly well-suited for the manufacture of knee spacers according to the invention.

Moreover, the invention can provide the tibial component to comprise a stem that extends from a central position of the side of the tibial component opposite from the running surface at an angle of between 85° and 90° with respect to the running surface, preferably extends perpendicular to the running surface. Preferably, the stem is intended for anchoring in a recess in the tibia. It is also preferred for the stem to be cylindrical and to comprise an external thread.

The stem serves for anchoring in the tibia. This allows a particularly stable connection to the tibia to be attained. Moreover, the external thread can be used for variable and stable adjustment of the distance between the contact surface of the separator and the running surface of the tibial component.

The invention can just as well provide multiple separators to be arranged on the contact surface of the tibial component, whereby the separators preferably extend from the anchoring surface such as to be convergent, at least over regions thereof, and whereby the stem particularly preferably is at least four times as high as the separators of the contact surface of the tibial component.

The purpose of the separators is to have a sufficient amount and a sufficiently thick layer of bone cement for connecting the two components to the bone remain and to thus generate a stable connection of the components to the bones.

The objects of the invention are also solved by a method for adapting a knee spacer to a treatment scenario, in particular a knee spacer of the type described above, comprising a tibial component and a separator, whereby the tibial component comprises a running surface for placing against a femoral component in mobile manner, and the separator comprises a contact surface for placing on the tibia, whereby the method involves adjusting the distance between the contact surface and the running surface.

In this context, the invention can provide the distance between the contact surface and the running surface to be adjusted by rotating the separator on a stem having an external thread, whereby the stem is affixed on the side of the tibial component opposite from the running surface, and the separator comprises at least one opening having an internal thread such that the separator can be screwed onto the stem by rotating the separator.

And lastly, the objects of the invention are also met through the use of a knee spacer of this type as temporary place-holder in a knee of a patient.

The invention is based on the surprising finding that the use of a variable separator allows a knee spacer and/or a tibial component for a knee spacer to be provided that can be stably placed and affixed on a tibial plateau and can concurrently be used to replace a variable length of a missing piece of tibia removed earlier. The knee spacer and/or the tibial component can therefore be used for temporary replacement of a knee joint independent of the extent to which the tibia was removed down to the tibial plateau thus produced. Simultaneously, the tibial component can also be placed on the tibial plateau in very stable manner without having to worry that it might tilt or that the bone cement might be pressed out while the bone cement used to affix the tibial component cures. Accordingly, the tibial component is safe from tilting and easy to position.

A knee spacer system according to the invention is composed of at least one femoral component, one tibial component, and one separator.

Preferably, the knee spacer system is characterised in that
a) a stem containing at least one external thread is arranged on the distal side of the tibial component, and
b) in that a separator containing a recess whose inside has at least one internal thread arranged on it is arranged appropriately in rotatable manner such that the distance between the distal side of the tibial component and the proximal side of the separator can be adjusted by rotating the separator on the stem.

The tibial component of primary knee joint endoprostheses usually possesses on its distal side a stem that is approximately two to five centimeters in length and is needed for anchoring the tibial component in the proximal tibia. This means that there is a cavity in the proximal tibia approximately 2 to 5 cm in depth after removal of the tibial component during revision surgeries. As a result, a stem at the distal side can also be provided on the tibial component of the knee spacer system.

According to the invention, the separator is provided as a disc, whereby the proximal and the distal side of the separator are preferably planar, particularly preferably are plane-parallel.

The separator preferably contains one or more opening(s) which connect the distal and the proximal side of the separator. This means that the medical user can easily introduce polymethylmethacrylate bone cement through said openings into the space between the separator and the distal side of the tibial component such that said space is filled completely. This ensures a secure connection and thus the transmission of force between the tibial component and the separator. The tibial component gets connected to the separator such that a uniform component is formed. Polymethylmethacrylate bone cement is also applied on the distal side of the separator and this cement layer is used to affix the composite component consisting of the tibial component and the separator to the proximal tibia.

The knee spacer system consists of a biocompatible material. The knee spacer system preferably consists of cured polymethylmethacrylate bone cement containing at least one antibiotic and/or at least one antiseptic. All antibiotics that are common in orthopaedics are conceivable as antibiotics in this context. Gentamicin, tobramycin, clindamycin, vancomycin, daptomycin, and fosfomycin are particularly well-suited. All other anti-infective substances are also well-suited. It is also possible for the polymethylmethacrylate bone cement to contain antiseptics. In this context, in particular polyhexanide, octenidine, and hydrogen peroxide-releasing substances, such as calcium peroxide, urea-hydrogen peroxide adduct are conceivable.

The scope of the invention also includes a method that is characterised in that the distance between the distal side of the tibial component and the proximal side of the separator is being adjusted by rotating the separator on the thread of the stem.

The knee spacer according to the invention is used as temporary place-holder in the scope of two-stage septic revision surgeries of knee endoprostheses.

Figure 2:
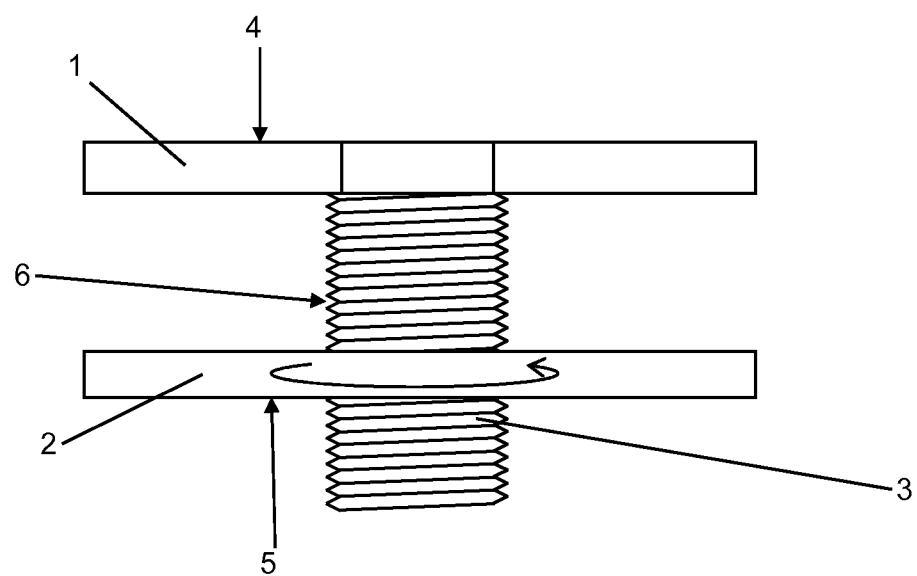
Figure 3:
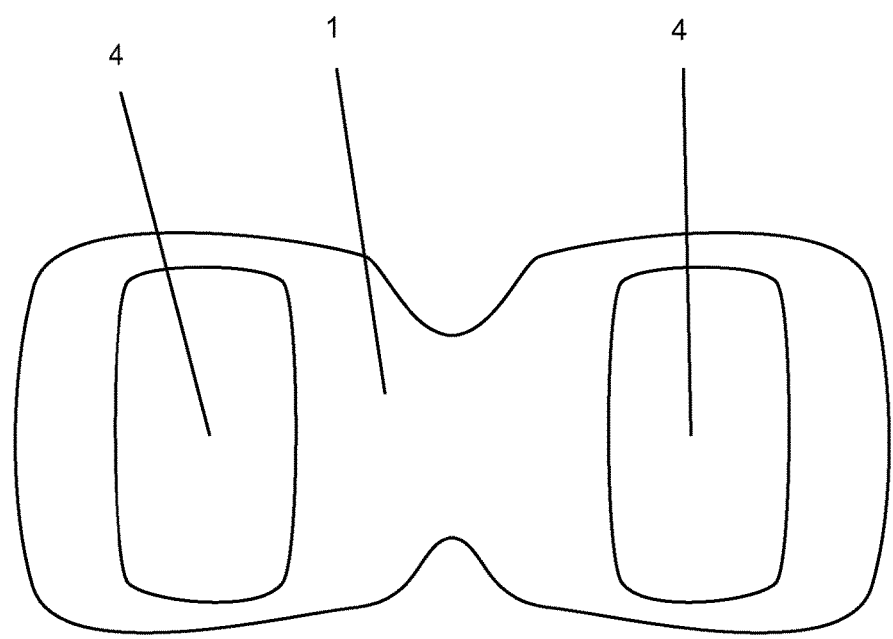
Figure 4:
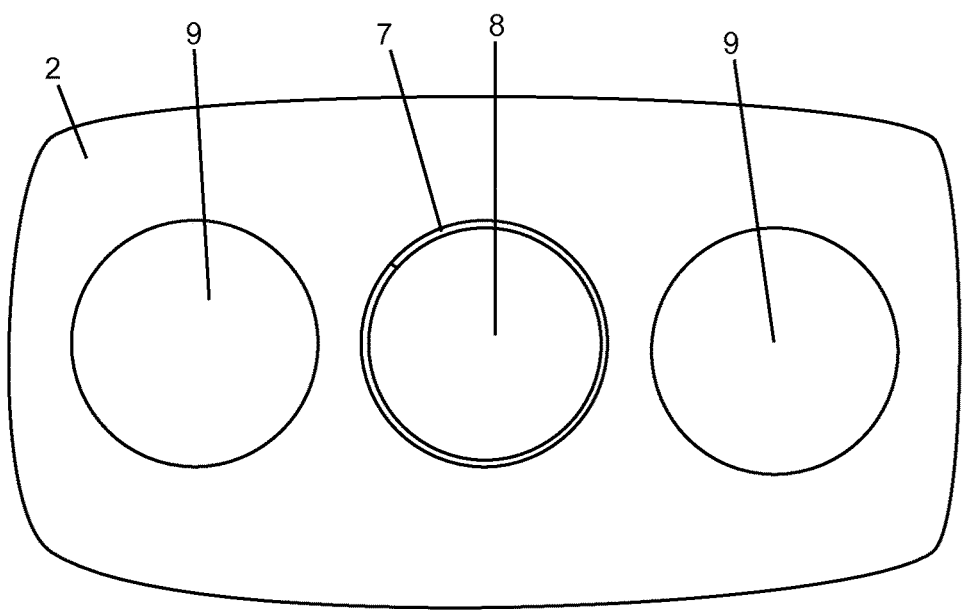
Figure 5:
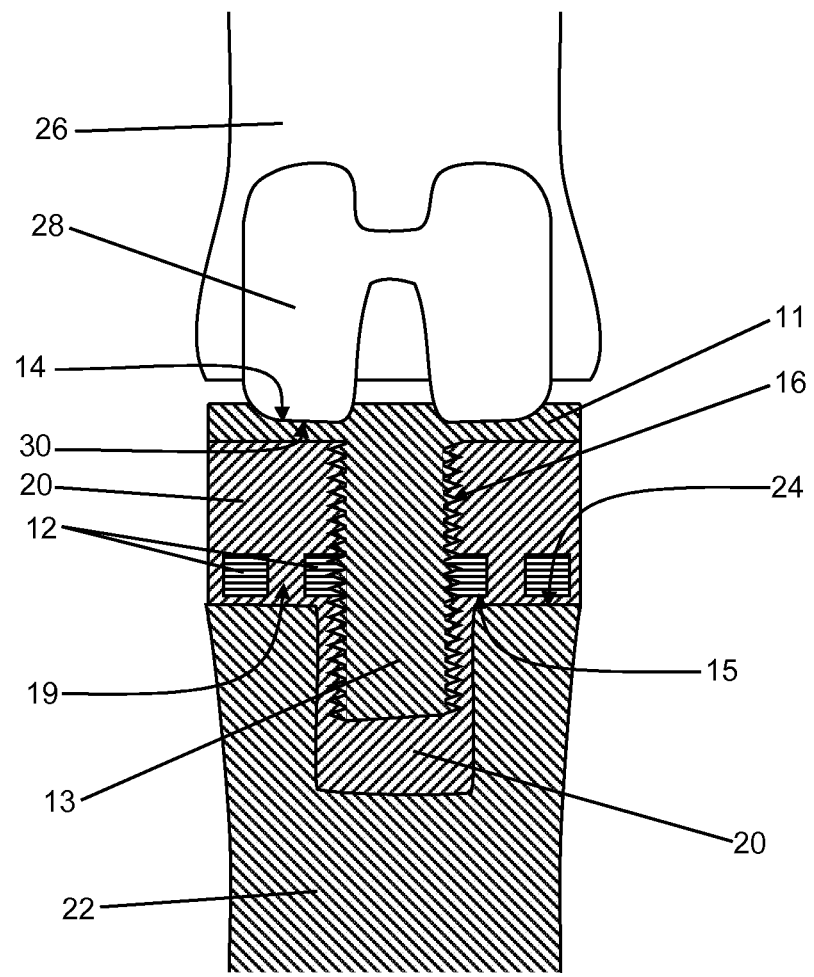

Exemplary embodiments of the invention shall be illustrated in the following on the basis of five schematic figures, though without limiting the scope of the invention. In the figures:

FIG. 1: shows a schematic side view of a knee spacer according to the invention;

FIG. 2: shows a schematic side view of a knee spacer according to the invention, in which the separator is screwed onto the tibial component;

FIG. 3: shows a schematic top view onto the running surface of a tibial component for a knee spacer according to the invention;

FIG. 4: shows a schematic top view onto a separator for a knee spacer according to the invention; and FIG. 5: shows a schematic partially cross-sectional view of a knee spacer according to the invention comprising a tibial component, a femoral component, and a separator.

To some extent, identical or similar components are identified in the figures through the same reference numbers.

FIG. 1 shows a schematic side view of a knee spacer according to the invention. The knee spacer comprises a tibial component 1 and a separator plate 2 that are fabricated from cured PMMA bone cement containing at least one antibiotic and/or at least one antiseptic. The tibial component 1 consists of an anatomically fitting plate and a cylindrical stem 3 that is arranged on the underside of the plate (on the bottom in FIG. 1). A running surface 4 is provided on the upper side of the plate of the tibial component 1 and is intended to serve as sliding surface for a running surface of a femoral component (not shown in FIG. 1).

The separator 2 is formed by a plane-parallel plate on the underside of which the contact surface 5 for placing on the tibial plateau is provided. The stem 3 comprises an external thread 6 that matches an internal thread 7 in a feed-through of the separator 2 (indicated by a dotted line in FIG. 1, since the internal thread 7 is actually not visible from the side). The separator 2 can be screwed onto the stem 3 by this means.

FIG. 2 shows a schematic side view of the knee spacer according to FIG. 1, in which the separator 2 is screwed onto the tibial component 1 or the stem 3, as the case may be. The distance between the contact surface 5 of the separator 2 and the running surface 4 of the tibial component 1 can be adjusted by rotating the separator 2 about the axis of the stem 3. A rotation as indicated by the arrow in FIG. 2 displaces the separator 2 in the direction of the plate of the tibial component 1 and thus shortens the distance between the contact surface 5 and the running surface 4. Theoretically, a left-handed thread could just as well be arranged on the stem 3 and would invert the direction of rotation.

FIG. 3 shows a schematic top view onto the running surface 4 of a tibial component 1 for a knee spacer according to the invention. For this purpose, the running surface 4 is designed to have a smooth surface such that a running surface of a femoral component can slide well over the running surface 4 of the tibial component 1.

FIG. 4 shows a schematic top view onto a separator 2 for a knee spacer according to the invention. A central feed-through 8 is arranged in the separator 2 and has the internal thread 7 arranged in it. Designed as a plane-parallel plate, the separator 2 further comprises two more bore holes 9 that are arranged on both sides of the feed-through 8 having the internal thread 7 and extend fully through the separator 2. During insertion of the separator 2 into a knee of a patient, the separator 2 is affixed by bone cement on an artificially generated tibial plateau. In this context, the bone cement can flow through the bore holes 9 and anchors the separator 2 on the tibia once the bone cement is cured.

FIG. 5 shows a schematic partially cross-sectional view of a knee spacer according to the invention or of a knee spacer system, as the case may be, comprising a tibial component 11, a femoral component 28, and a separator 12. The plate-shaped separator 12 screwed onto the tibial component 11 comprises, on its underside (on the bottom in FIG. 5), a contact surface 15 that is placed on a tibial plateau 24 of a tibia 22 (shin bone) and is affixed and/or embedded by means of bone cement 20.

The whole part of the knee spacer relating to the tibia 22 and the tibia 22 itself are shown in a cross-sectional view, whereby the sectioned surfaces are indicated by hatching. The section is placed in a plane perpendicular to the sagittal plane and/or parallel to or in the frontal plane. The cross-sectional view enables depiction of the internal structure of the tibial component 11 and its anchoring. In contrast, the femoral component 28, which is affixed to a femur 26 of the patient by means of bone cement, is shown in a side view.

The femoral component 28 comprises a rounded running surface 30 that can slide or roll off on the running surface 14 of the tibial component 11. As a result, an articulating two-part knee spacer is provided. A recess for accommodating the stem 13 is provided in the tibia 22. Depending on the amount of bone removed from the tibial plateau 24 of the tibia 22, the original position of the running surface 14 of the knee can be restored by screwing the separator 12 up to a certain height onto an external thread 16 of the stem 13. The separator 12 comprises a feed-through with a fitting internal thread for this purpose. By this means, it is feasible through little effort to adjust the distance between the running surface 14 of the tibial component 11 and the contact surface 15 of the separator 12 relatively accurately and thus to enable relatively accurate adjustment of the position of the artificial knee joint.

The circular separator 12 has multiple bore holes 19 provided in it through which the bone cement 20 extends and thus stably connects and/or anchors the separator 12 and the tibial component 11 to the tibia 22.

During a revision surgery of an artificial knee joint, the position of the joint of the articulating knee spacer can be adjusted by rotating the separator 12 on the stem 13 for the surgery following debridement of the tibial bone 22. Once the required distance between the contact surface 15 of the separator 12 and the running surface 14 of the tibial component 11 is adjusted, the tibial component 11 with the separator 12 is cemented onto the tibial plateau 24 using PMMA bone cement 20 and the intervening spaces between the tibial component 11 and the separator 12 as well as the bore holes 19 are filled up with the same PMMA bone cement 20. Likewise, the femoral component 28 is affixed on the femur 26 using the same PMMA bone cement.

The knee spacer is thus inserted and functionally ready. If the parts 11, 12, 28 of the knee spacer and the bone cement 20 contain at least one antibiotic and/or antiseptic, the knee spacer can be used to control a site of infection in the knee.

Knee spacers and/or the components 1, 2, 18 thereof preferably have rounded corners and edges rather than sharp edges and corners.

The features of the invention disclosed in the preceding description and in the claims, figures, and exemplary embodiments, can be essential for the implementation of the various embodiments of the invention both alone and in any combination.

LIST OF REFERENCE NUMBERS

1 Tibial component
2 Separator plate
3 Stem
4 Running surface
5 Contact surface
6 External thread
7 Internal thread
8 Feed-through
9 Bore hole
11 Tibial component
12 Separator plate
13 Stem
14 Running surface
15 Contact surface
16 External thread
19 Bore hole
20 PMMA bone cement
22 Tibia
24 Tibial plateau
26 Femur 28 Femoral component
30 Running surface

The invention claimed is:

1. A knee spacer for temporary replacement of an artificial knee joint, whereby the knee spacer comprises a femoral component comprising a sliding surface, a tibial component and a separator, whereby the tibial component comprises a sliding surface by means of which the tibial component, in a patient-inserted state, is adapted to be placed against the femoral component in mobile manner, and whereby the separator comprises a contact surface for placing on a tibia and the contact surface is adjustable at a variable distance from the sliding surface of the tibial component,
- wherein one or more opening(s) are situated in the contact surface of the separator through which a bone cement can extend by means of which the separator is affixed on the tibia,
- and a layer of bone cement is arranged between the contact surface and the tibia's tibial plateau.

2. The knee spacer according to claim 1, wherein a stem with an external thread is arranged on a side of the tibial component opposite from the sliding surface of the tibial component, whereby the separator comprising at least one feed-through is adapted to be screwed onto the stem by means of an internal thread that fits with the external thread of the stem such that the distance between the sliding surface of the tibial component and the contact surface is adjustable by screwing the separator onto the stem.

3. The knee spacer according to claim 1, wherein the femoral component and the tibial component are present as separate components, which are mobile with respect to each other in the patient-inserted state, whereby the tibial component and the femoral component are placed against each other in mobile manner in the patient-inserted state by means of their sliding surfaces.

4. The knee spacer according to claim 1, wherein the separator comprises a disc, preferably a plane-parallel disc, whereby one side of a disc forms the contact surface.

5. The knee spacer according to claim 1, wherein the knee spacer comprises a biocompatible material.

6. A method for adapting a knee spacer according to claim 1 to a treatment scenario, whereby the method comprises a step of adjusting a distance between the contact surface and the sliding surface of the tibial component.

7. The method according to claim 6, wherein the distance between the contact surface and the sliding surface of the tibial component is adjusted by rotating the separator on a stem having an external thread, whereby the stem is affixed on a side of the tibial component opposite from the sliding surface of the tibial component and the separator comprises at least one feed-through having an internal thread such that the separator is screwed up or down on the stem by rotating the separator.

8. The knee spacer according to claim 5 wherein the knee spacer comprises a cured polymethylmethacrylate bone cement containing at least one antibiotic, or at least one antiseptic, or both at least one antibiotic and at least one antiseptic.

9. A method for adapting a knee spacer to a treatment scenario, wherein the knee spacer comprises a femoral component comprising a sliding surface, a tibial component and a separator, whereby the tibial component comprises a sliding surface for placing against the femoral component in mobile manner in a patient-inserted state, and the separator comprises a contact surface for placing on a tibia and one or more openings which connect distal and proximal side of the separator,
- whereby the method comprises a step of adjusting a distance between the contact surface and the sliding surface of the tibial component, and a step of introducing bone cement through the one or more openings into a space between the separator and a distal side of the tibial component such that said space is filled completely and the tibial component is connected to the separator.

* * * * *